US008505782B1

(12) United States Patent
Gardiner et al.

(10) Patent No.: US 8,505,782 B1
(45) Date of Patent: Aug. 13, 2013

(54) METHOD AND APPARATUS FOR DISPENSING SANITIZER FLUID

(75) Inventors: Virginia Gardiner, London (GB); Jacob McKnight, Argyll (GB); Adam Tavin, East Palo Alto, AZ (US); George W. Heropoulos, Gilroy, CA (US); Alexander R. Oshmyansky, Boston, MA (US); Dan Nicolau, Berkeley, CO (US)

(73) Assignee: Altitude Medical Inc., Boston, MA (US)

( * ) Notice: Subject to any disclaimer, the term of this patent is extended or adjusted under 35 U.S.C. 154(b) by 189 days.

(21) Appl. No.: 12/930,603

(22) Filed: Jan. 11, 2011

Related U.S. Application Data

(60) Provisional application No. 61/335,717, filed on Jan. 11, 2010.

(51) Int. Cl.
*B67D 1/07* (2006.01)
*A61L 2/00* (2006.01)

(52) U.S. Cl.
USPC ..................... 222/192; 222/181.3; 222/321.7; 422/292; 422/300

(58) Field of Classification Search
USPC ................ 222/192, 207, 402.1, 321.1, 321.7, 222/1, 180, 181.3, 323, 324; 422/292, 300, 422/306, 123
See application file for complete search history.

(56) References Cited

U.S. PATENT DOCUMENTS 3,967,478 A 7/1976 Guinn
4,046,508 A 9/1977 McDonald
4,710,634 A 12/1987 Brookes
4,896,144 A 1/1990 Bogstad
4,997,139 A * 3/1991 Menard ......................... 242/535
5,454,409 A 10/1995 McAffer et al.
5,808,553 A 9/1998 Cunningham
6,029,600 A * 2/2000 Davis ............................ 116/200
6,211,788 B1 4/2001 Lynn et al.
6,289,557 B1 * 9/2001 Manson et al. ................. 16/412
6,577,240 B2 6/2003 Armstrong
6,645,435 B2 11/2003 Dawson et al.

(Continued)

FOREIGN PATENT DOCUMENTS

DE 198 57 268 A1 6/2000
WO WO 2007/107784 A2 9/2007

OTHER PUBLICATIONS

International Search Report and Written Opinion dated Nov. 12, 2008 for PCT Application No. PCT/US2008/006505.

(Continued)

*Primary Examiner* — Kevin P Shaver
*Assistant Examiner* — Stephanie E Williams
(74) *Attorney, Agent, or Firm* — Moser Taboada

(57) ABSTRACT

A method and apparatus for dispensing sanitizer fluid. The apparatus includes a handle having a trigger lever and a spray nozzle; a check valve coupled to the spray nozzle; a pump assembly fluidly coupled to the check valve; and a reservoir cartridge fluidly coupled to the pump assembly, where manipulation of the handle and the trigger lever causes the pump assembly to supply sanitizer fluid from the cartridge, through the check valve, and to the nozzle. A method of selectively dispensing sanitizer fluid includes selectively manipulating a handle to manipulate a door latch or manipulating a handle and a trigger lever to manipulate a door latch and dispense sanitizing fluid through a spray nozzle proximate the trigger lever.

14 Claims, 5 Drawing Sheets

(56) References Cited

U.S. PATENT DOCUMENTS

| | | | | |
|---|---|---|---|---|
| 6,874,697 | B2 | 4/2005 | Callueng | |
| 7,080,427 | B1 * | 7/2006 | Campopiano et al. | 16/110.1 |
| 7,320,418 | B2 * | 1/2008 | Sassoon | 222/649 |
| 7,338,646 | B2 * | 3/2008 | Gilbert | 422/292 |
| 2004/0223894 | A1 | 11/2004 | Gilbert | |
| 2006/0153733 | A1 | 7/2006 | Sassoon | |
| 2006/0245818 | A1 | 11/2006 | Stropkay et al. | |

OTHER PUBLICATIONS

International Preliminary Report on Patentability dated Dec. 17, 2009 for PCT Application No. PCT/US2008/006505.

Supplementary European Search Report mailed Jun. 6, 2011 for Application No. 087546180.0-2113/2155266 (PCT/US2008006505).

* cited by examiner

METHOD AND APPARATUS FOR DISPENSING SANITIZER FLUID

CROSS-REFERENCE TO RELATED APPLICATIONS

This application claims benefit of U.S. provisional patent application Ser. No. 61/335,717, filed Jan. 11, 2010, which is herein incorporated by reference.

BACKGROUND OF THE INVENTION

1. Field of the Invention

Embodiments of the present invention generally relate to health care technology and, in particular, to a method and apparatus for dispensing sanitizer fluid through a door handle.

2. Description of the Related Art

Prevention of harmful diseases is a major concern for governments as well as various enterprises, such as multi-national corporations. If these diseases are not contained, an epidemic may ensue resulting in widespread panic and disorder among the population. For example, health care facilities, such as hospitals, may be overrun with patients straining the available medical professional workforce. In order to ensure a productive work and living environment, various enterprises and governments use various health care technologies, such as a sanitizer fluid, to stop the spread of pathogens that cause the harmful diseases. Such sanitizer fluids are generally dispensed via pump canisters located in bathrooms or via wall mounted pump canisters distributed throughout a building. Such sanitizer availability may not be convenient nor does availability guarantee use of the sanitizer fluid.

Therefore, there is a need in the art for a method and apparatus for dispensing sanitizer fluid in a very convenient manner, via door handles such that sanitizer fluid is conveniently available throughout a building.

SUMMARY

Embodiments of the present invention comprise a method and apparatus for dispensing sanitizer fluid. The apparatus comprises a handle having a trigger lever and a spray nozzle; a check valve coupled to the spray nozzle; a pump assembly fluidly coupled to the check valve; and a reservoir cartridge fluidly coupled to the pump assembly, where manipulation of the handle and the trigger lever causes the pump assembly to supply sanitizer fluid from the cartridge, through the check valve, and to the nozzle.

A method of selectively dispensing sanitizer fluid comprises selectively manipulating a handle to manipulate a door latch or manipulating a handle and a trigger lever to manipulate a door latch and dispense sanitizing fluid through a spray nozzle proximate the trigger lever.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
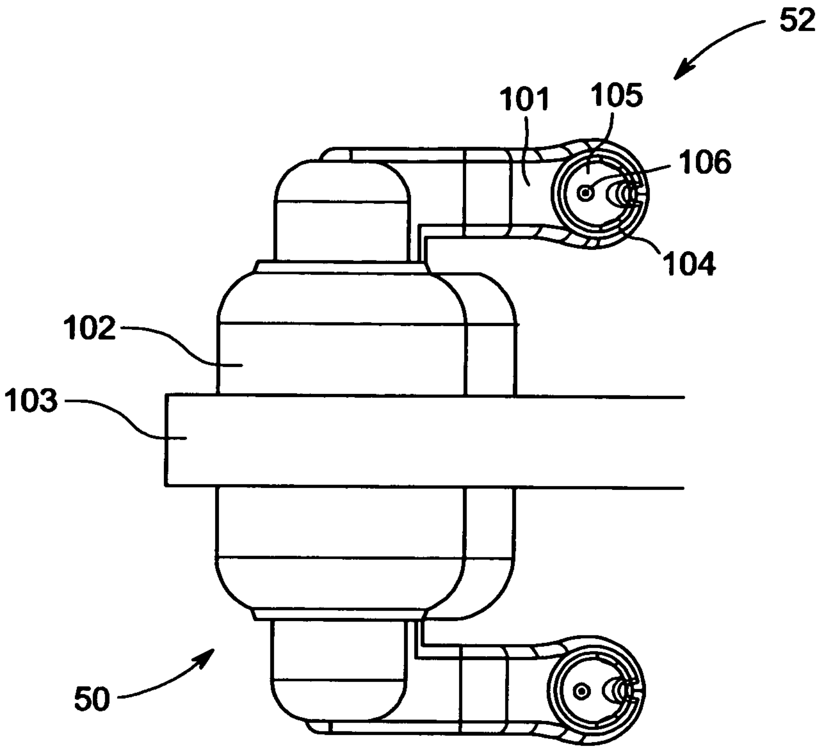
FIG. 1 depicts a plan view of one embodiment of the present invention with a door having two door handle devices mounted on either side of a conventional door.

FIG. 1 is a plan view of one embodiment of the present invention comprising a pair of sanitizer fluid dispensing devices 50 and 52 (hereinafter devices 50 or 52) mounted on each side of a conventional door 103. The devices 50 and 52 are substantially identical in construction and operation; however, the devices the structure of each is mirror image of the other to facilitate mounting on opposite sides of the door 103.

Each device 50 and 52 comprises a handle 101 coupled to a handle base 102. The handle base 102 is connected to the door 103. Rotating the handle 101 operates a conventional door latch (not shown) to release the latch to facilitate opening the door. A trigger lever 104 forms a "horse-shoe shape" around a spray cone 105 at the end of the door handle 101. At the center point of the spray cone 105, a spray nozzle 106 is positioned to release sanitizer fluid. A trigger lever 104 controls the dispensing of sanitizer fluid onto a hand as the hand manipulates the handle 101. Although foaming sanitizer liquid is described as used in one embodiment of the invention, other types of sanitizing fluids based on or containing compounds with antibacterial, anti-viral, and/or anti-fungal properties, including but not limited to, ones based on: alcohol; benzochloronate; iodine; silver; silver-nitrate; TRIOSYN; and zinc, as well as combinations and compounds thereof may be dispensed in various forms by the handle 101, including but not limited to, liquids, aerosols, sprays, streams and/or the like.

Figure 2:
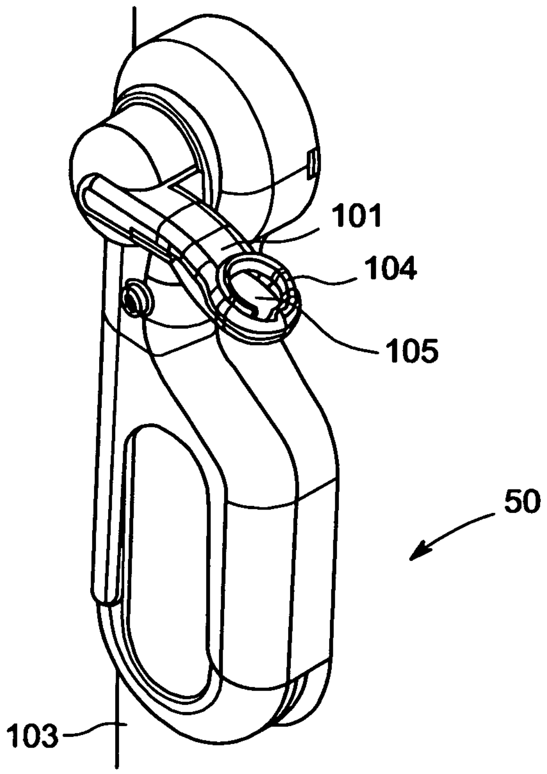
FIG. 2 depicts a perspective view of one embodiment of the present invention with the door handle device mounted on a door.

FIG. 2 depicts a perspective view of a device 50 mounted on a door 103. If the handle 101 is turned while the trigger lever 104 is depressed, the sanitizer fluid will be sprayed through the nozzle (not visible) that is situated in the spray cone 105. Thus, a user of may selectively receive sanitizer fluid upon their hand as they rotate the handle 101 to open the door.

Figure 3:
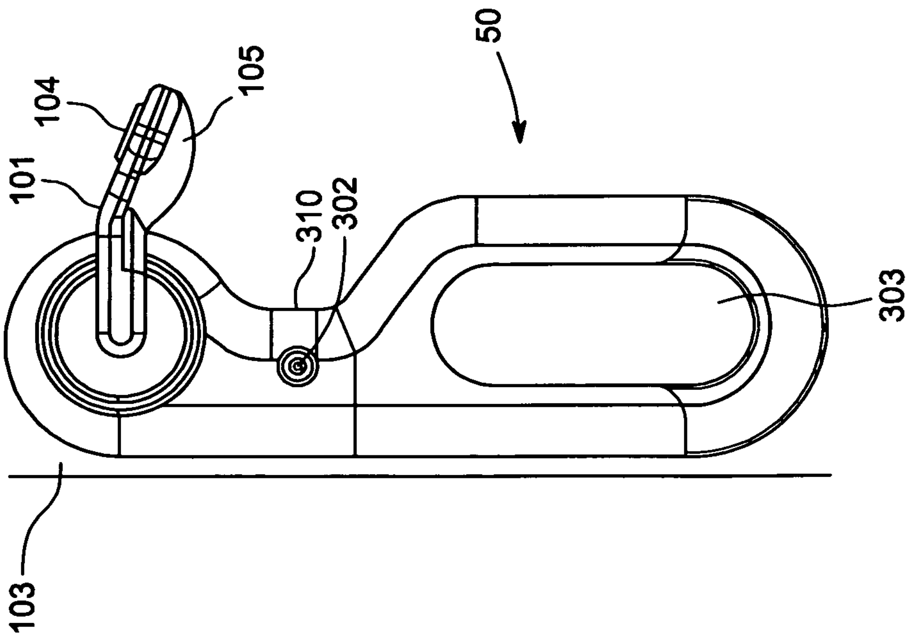
FIG. 3 depicts a front elevation view of one embodiment of the present invention with the door handle device mounted on a door.

FIG. 3 depicts a front elevation view of a device 50 that is mounted to a door 103. The spray cone 105 and trigger lever 104 can be seen at the end of the door handle 101. The neck 310 of the device 50 features a locking key 302 that allows a sanitizer fluid reservoir cartridge 303 to be removed and replaced when empty (i.e., the cartridge 303 is replaceable).

Figure 4:
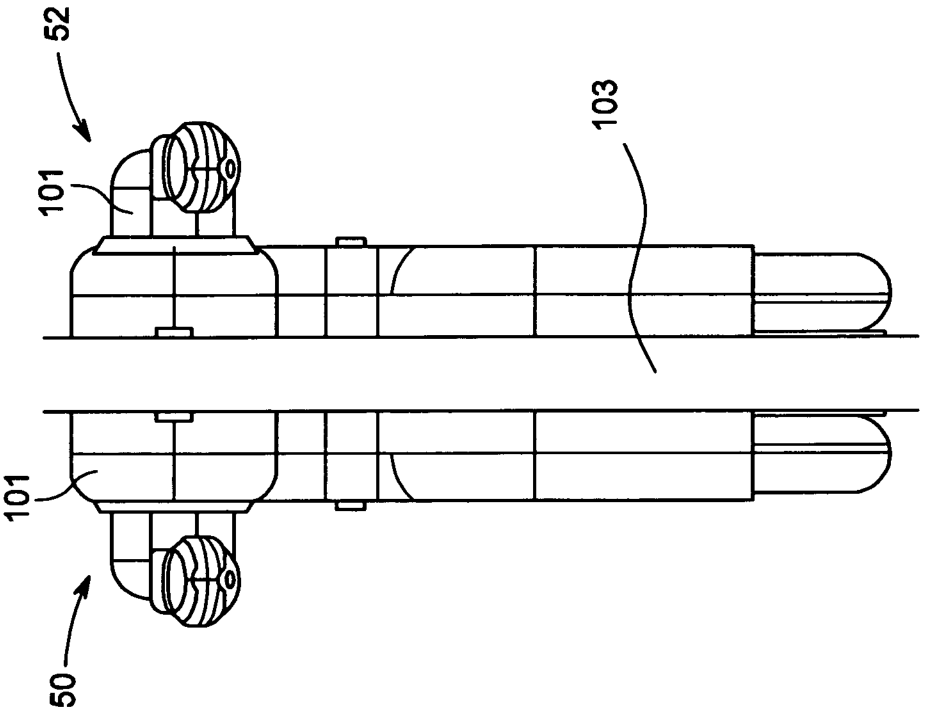
FIG. 4 depicts a side elevation view of one embodiment of the present invention with a door handle device mounted on each side of a door.

FIG. 4 depicts a side elevation view of the two devices 50 and 52 mounted on a door 103. The handles 101 are linked by a spindle (not visible) which passes through the conventional latch mechanism of the door 103. Thus, rotation of either handle actuates the latch mechanism in a conventional manner to unlatch the door and facilitate opening thereof.

Figure 5:
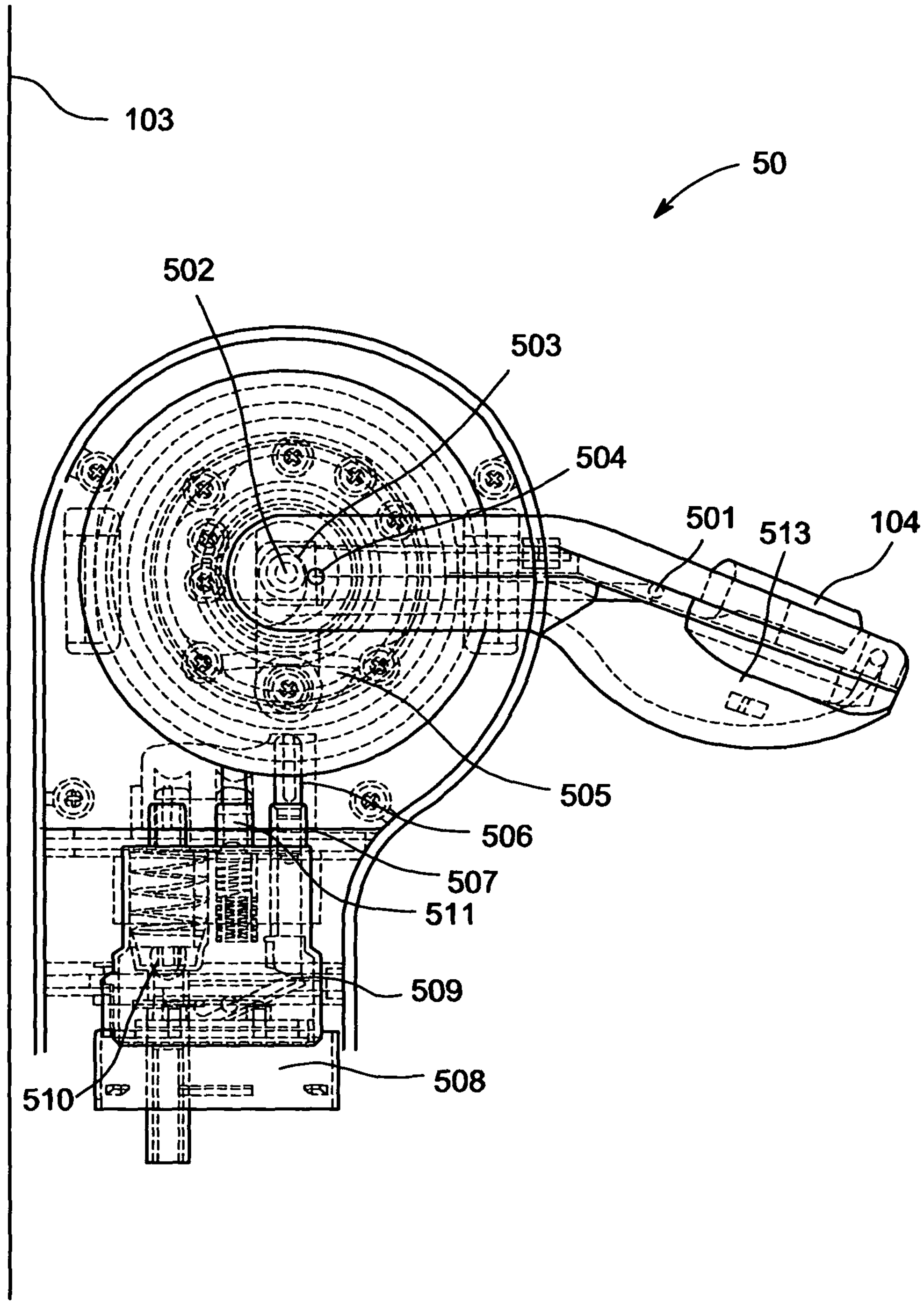
FIG. 5 depicts a sectional view of one embodiment of the present invention with all hidden detail shown.

FIG. 5 depicts a detailed sectional view of the devices 50 and 52. As a hand turns the handle 101, such as a twist latch handle, and opens the door 301, the trigger lever 104 may be depressed. The trigger lever 104 rotates around a fulcrum point 501 to provide rotational movement of a magnet 502 at the end of the trigger lever 104. As the trigger lever 104 is depressed, the trigger lever 104 rotates about fulcrum point 501 and the magnet 502 causes a magnetic check valve 503 to open. The rotation of the handle 101 about the spindle 504, also causes a rotating cam 505 to depress a push rod 506 that slides into the push rod port 507 of the reservoir cartridge cap 508 (see FIG. 6 for detail). The push rod 506 pushes one end of a see-saw lever 509 within the reservoir cartridge cap 508. The other end of this see-saw lever 509 pushes upward on a displacement pump 510 also fitted into the reservoir cartridge cap 508. This movement causes the displacement pump 510 to be compressed, forcing the sanitizer fluid inside the pump to be pushed up through a tube (not pictured) into the magnetic check valve 503. If the trigger lever 104 is depressed and the magnetic check valve 503 is open, hand sanitizer fluid passes through the magnetic check valve 503 to the nozzle 106 at the base of the spray cone 105. The sanitizer fluid is released (i.e., sprayed) upward onto the hand of the user operating the handle 101. If the trigger lever 104 is not depressed, the magnetic check valve 503 remains closed and the liquid returns to the reservoir cartridge 303 via the return port 511 in the reservoir cartridge cap 508.

Figure 6:
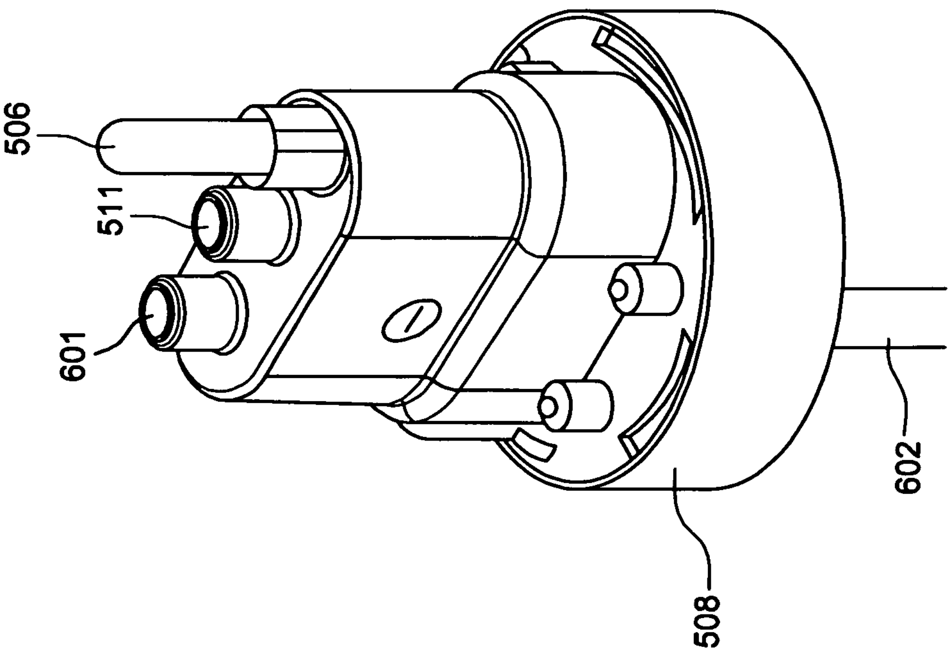
FIG. 6 shows a perspective view of one embodiment of the present invention with the cap of the replaceable cartridge.

FIG. 6 features a perspective view of the reservoir cartridge cap 508. The top of the push rod 506 is located alongside the return port 511 and the pump exit port 601. The dip-tube 602 emerges from the other side of the cap 508. The dip tube 602 extends into a sanitizer fluid reservoir cartridge 303 (FIG. 3) to facilitate extraction of the sanitizer fluid.

Figure 7:
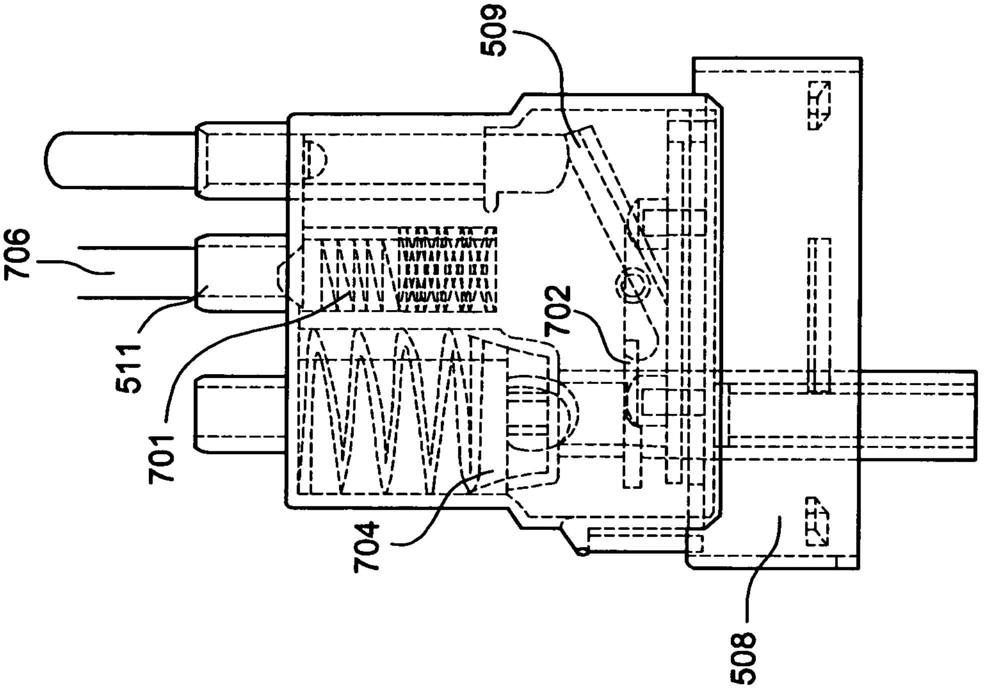
FIG. 7 depicts a sectional view of one embodiment of the present invention with all hidden detail of the replaceable cartridge cap shown.

FIG. 7 depicts a front elevation of the reservoir cartridge cap 508 with all internal detail revealed. The return port 511 features a spring valve 701 that allows fluid to flow back into the reservoir cartridge only when sufficient pressure is generated by the pumping action of the handle 101 being rotated. This increased pressure in the tube 706 attached to return port 511 forces the spring valve 701 open and allows sanitizing fluid to return to the reservoir cartridge 303. The see-saw lever 509 meets a flange 702 on the base of a pump 704. The end of the see-saw lever 509 pushes against the flange 702 when the handle 101 is turned.

Figure 8:
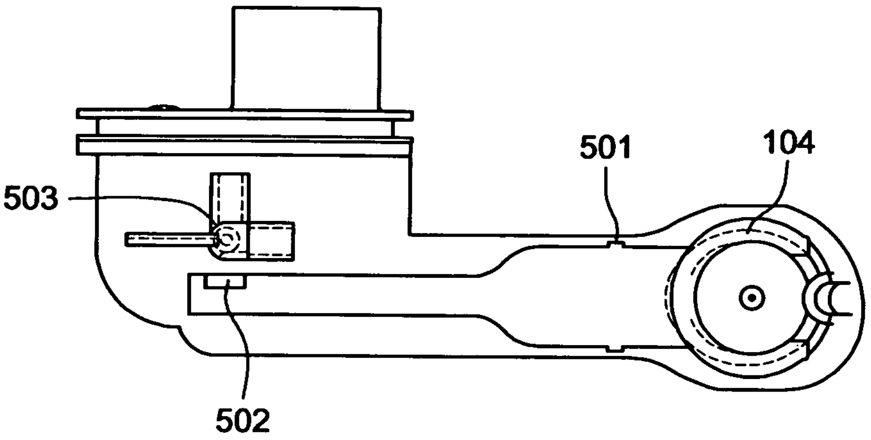
FIG. 8 shows a plan view of one embodiment of the handle lever.

FIG. 8 depicts a plan view of the device 50. The trigger lever 104 detail is visible and the fulcrum points 501 about which the trigger lever 104 rotates are shown. The drawing also shows the location of the magnet 502 which controls the magnetic ball valve 503.

Figure 9:
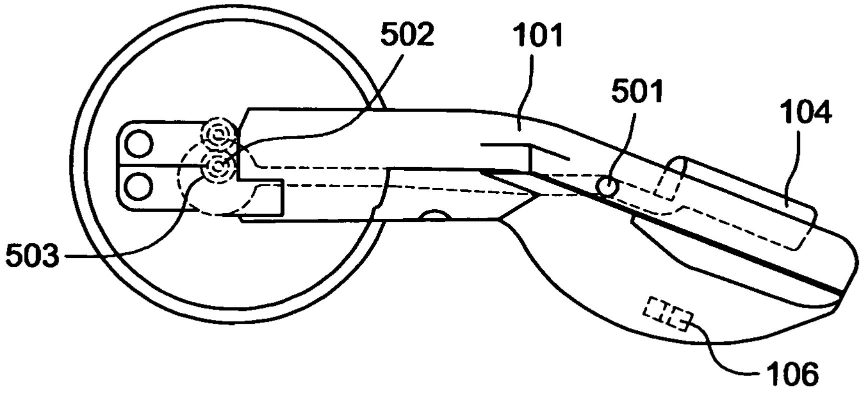
FIG. 9 shows a front elevation view of one embodiment of the handle lever.

FIG. 9 depicts a front elevation of the handle 101 showing detail of the trigger lever 104 and the magnet 502 at the base end of the trigger lever 104. The trigger lever does not apply force to any mechanism and is held only by the fulcrum connections 501. As such, there is very little resistance to the depression of the trigger lever 104 meaning that the natural griping of the handle 101 to open the door 103 is sufficient to open the magnetic ball valve 503 and to allow fluid to pass to the nozzle 106, spraying the hand.

Figure 10:
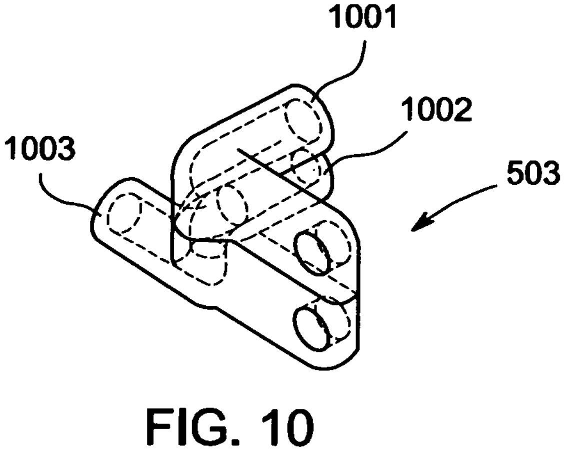
FIG. 10 shows a view of one embodiment of the present invention with a magnetic valve which controls the flow of sanitizing fluid from the reservoir to the handle.

FIG. 10 depicts the magnetic ball valve 503. The input port 1001 is above the reservoir return port 1002, while the handle port 1003 is perpendicular to these two ports 1001 and 1002. When a magnetic ball is covering the reservoir return port 1002 the sanitizing fluid can only flow to the handle port 1003. When the magnetic ball is covering the handle port 1003, the sanitizing fluid can only flow to the reservoir return port 1002.

While the foregoing is directed to embodiments of the present invention, other and further embodiments of the invention may be devised without departing from the basic scope thereof, and the scope thereof is determined by the claims that follow.

The invention claimed is:

1. An apparatus for dispensing sanitizer fluid comprising:

a manually operable door handle comprising a trigger lever and a spray nozzle, wherein the handle and trigger lever are independently operable;

a check valve coupled to the spray nozzle;

a pump assembly fluidly coupled to the check valve; and a reservoir cartridge fluidly coupled to the pump assembly, where manipulation of the handle and the trigger lever causes the pump assembly to supply sanitizer fluid from the reservoir cartridge, through the check valve and to the nozzle.

2. The apparatus of claim 1, further comprising a base supporting the handle, pump assembly and cartridge.

3. The apparatus of claim 2, the handle further comprising a spindle coupling the handle to the base; and a fulcrum point.

4. The apparatus of claim 3, wherein the handle is rotatable about the spindle and the trigger lever is rotatable about the fulcrum point.

5. The apparatus of claim 4, wherein the rotation of the handle is adapted to manipulate a door latch and draw sanitizer fluid from the reservoir cartridge.

6. The apparatus of claim 4, wherein the rotation of the handle together with the rotation of the trigger lever is adapted to manipulate a door latch, draw sanitizer fluid from the cartridge and disperse sanitizer fluid through the spray nozzle.

7. The apparatus of claim 5, wherein the handle is coupled to a rotating cam that interacts with a pump, where rotation of the handle and the cam generates linear motion to actuate the pump to draw sanitizer fluid from the cartridge.

8. The apparatus of claim 6, wherein sanitizer fluid is returned to the cartridge when the handle is rotated without corresponding rotation of the trigger lever.

9. The apparatus of claim 6, wherein rotation of the trigger lever actuates a magnet to open the check valve to allow sanitizer fluid to be dispersed through the spray nozzle.

10. The apparatus of claim 1, wherein the sanitizer fluid is dispensed as at least one of a liquid, a aerosol, a spray, or a stream.

11. The apparatus of claim 1, wherein the sanitizer fluid comprises at least one of an anti-bacterial, anti-viral, or anti-fungal compound.

12. A method of selectively dispensing sanitizer fluid, comprising:

selectively manipulating a manually operable door handle to manipulate a door latch or manipulating a handle and a trigger lever, wherein the handle and trigger lever are independently operable, to manipulate a door latch and dispense sanitizing fluid through a spray nozzle located on the handle and proximate the trigger lever.

13. The method of claim 12 wherein the sanitizer fluid is dispensed as at least one of a liquid, a aerosol, a spray, or a stream.

14. The method of claim 12, wherein the sanitizer fluid comprises at least one of an anti-bacterial, anti-viral, or anti-fungal compound.

* * * * *